United States Patent [19]

Daw et al.

[11] Patent Number: 5,658,282
[45] Date of Patent: Aug. 19, 1997

[54] APPARATUS FOR IN SITU SAPHENOUS VEIN BYPASS AND LESS-INVASIVE VARICOSE VEIN TREATMENT

[75] Inventors: Derek J. Daw, Costa Mesa; George M. Acosta, Long Beach; John R. Brustad, Dana Point, all of Calif.

[73] Assignee: Endovascular, Inc., Costa Mesa, Calif.

[21] Appl. No.: 484,187

[22] Filed: Jun. 7, 1995

Related U.S. Application Data

[63] Continuation-in-part of Ser. No. 183,994, Jan. 18, 1994, Pat. No. 5,437,664, and a continuation-in-part of Ser. No. 315,074, Sep. 29, 1994, abandoned.

[51] Int. Cl.⁶ .................................................. A61B 17/32
[52] U.S. Cl. ............................... 606/49; 606/40; 606/42; 606/159; 606/170
[58] Field of Search .......................... 606/27–35, 37–42, 606/45–52, 159, 170, 167; 600/104, 108, 130, 153, 160

[56] References Cited

U.S. PATENT DOCUMENTS

| | | |
|---|---|---|
| 3,858,586 | 1/1975 | Lessen . |
| 4,016,881 | 4/1977 | Rioux et al. . |
| 4,057,063 | 11/1977 | Gieles et al. . |
| 4,126,137 | 11/1978 | Archibald . |
| 4,311,145 | 1/1982 | Esty et al. . |
| 4,416,276 | 11/1983 | Newton et al. . |
| 4,418,692 | 12/1983 | Guay . |
| 4,474,179 | 10/1984 | Koch . |
| 4,565,200 | 1/1986 | Cosman . |
| 4,658,819 | 4/1987 | Harris et al. . |
| 4,682,596 | 7/1987 | Bales et al. . |
| 4,907,589 | 3/1990 | Cosman . |
| 4,966,597 | 10/1990 | Cosman ............................ 606/50 |
| 4,998,933 | 3/1991 | Eggers et al. . |
| 5,057,105 | 10/1991 | Malone et al. . |
| 5,122,137 | 6/1992 | Lennox ............................ 606/40 |
| 5,122,138 | 6/1992 | Manwaring ....................... 606/46 |
| 5,133,725 | 7/1992 | Quadri ............................ 606/159 |
| 5,167,658 | 12/1992 | Ensslin . |
| 5,190,541 | 3/1993 | Abele et al. ...................... 606/46 |
| 5,267,994 | 12/1993 | Gentelia et al. .................. 606/46 |
| 5,304,190 | 4/1994 | Reckelhoff et al. ............... 606/170 |
| 5,370,645 | 12/1994 | Klicek et al. . |
| 5,498,258 | 3/1996 | Hakky et al. ..................... 606/170 |
| 5,527,331 | 6/1996 | Kresch et al. .................... 606/170 |

FOREIGN PATENT DOCUMENTS 93103063  2/1993  European Pat. Off. .

OTHER PUBLICATIONS

"Tissue Heating During Radiofrequency Catheter Ablation: AThermodynamic Model & Observations in Isolated Perfused & Superfused Canine Right Ventricular Free Wall." By Haines & Others, Pace, vol. 12, pp. 962–975, Jun. 1989.

"Home Hemodialysis," By Eschbach & Others, The Medical Letter on Drugs & Therapeutics, vol. 14, Issue 248, pp. 53–55, Jul. 12, 1968.

(List continued on next page.)

*Primary Examiner*—Angela D. Sykes
*Assistant Examiner*—Michael Peffley
*Attorney, Agent, or Firm*—John L. Rogitz

[57] ABSTRACT

An apparatus for in situ saphenous vein bypass includes an operating catheter which includes an optical fiber and an electrode, and a control catheter which includes a valvulotome. The operating catheter and control catheter are locked together and advanced through an incision in the leg. The catheters are closely spaced from each other, on opposite sides of a valve to be disrupted. Then, the valvulotome is manipulated to disrupt the valve, the electrode is manipulated to stanch blood flow from the valve and to close off side branches, and both procedures are viewed by means of the optical fiber. The valves of the saphenous vein are thusly disrupted in sequence, and the side branches to the saphenous vein closed off, to thereby modify the saphenous vein in situ for arterial use. In alternate embodiments, the electrode is used with delivery catheters to stop blood flow through a side branch or varicose vein. The electrode includes an embedded temperature sensor for sensing electrode temperature.

17 Claims, 6 Drawing Sheets

OTHER PUBLICATIONS

"Complications & Difficulties in Electrocoagulation of Varices of the Lower Extremities," By Politowsky & Others, Surgery vol. 59, No. 6, pp. 932–934, Jun. 1966.

"Technical Use of Transcatheter Electrocoagulation," by Michael D. Miller & others, Work In Progress, vol. 9.129, pp. 211–214, Oct. 1978.

"Vessel Occlusion with Transcatheter Electrocoagulation: Initial Clinical Experience[1]" Radiology, by William M. Thompson & others, vol. 133, pp. 335–340, Nov., 1979.

"Electrothrombosis as a Treatment of Cirsoid Angioma in the Face and Scalp and Varicosis of the Leg," By Ogawa & Inoue, Plastic & Reconstructive Surgery, vol. 70, No. 3, Sep., 1982.

"Ambulatory Stab Evulsion Phlebectomy for Truncal Varicose Veins," By Goren & Yellin, The American Journal of Surgery, vol. 162, pp. 166–174, Aug., 1991.

"Experimental Closure of Arteriovenous Fistula by Transcatheter Electrocoagulation[1]," Joseph F. Phillips & others, Radiology, vol. 115, pp. 319–321, May, 1975.

"The Mechanism Of Blood Vessel Closure By High Frequency Electrocoagulation," By Sigel & Dunn, Surgery, Gynecology & Obstetrics, pp. 823–831, Oct., 1965.

"A Bipolar Electrode for Vascular Electrocoagulation with Alternating Current[1]," By Brunelle & others, Radiology, vol. 137, pp. 239–240, Oct., 1980.

"Catheter for Endoluminal Bipolar Electrocoagulation[1]," By Becker & others, Radiology, vol. 170, pp. 561–562, Nov., 1989.

RFG–3C RF Lesion Generator System, Radionics, P.O. Box 438, 76 Cambridge Street, Burlington, Mass. 01803–0738, 1990.

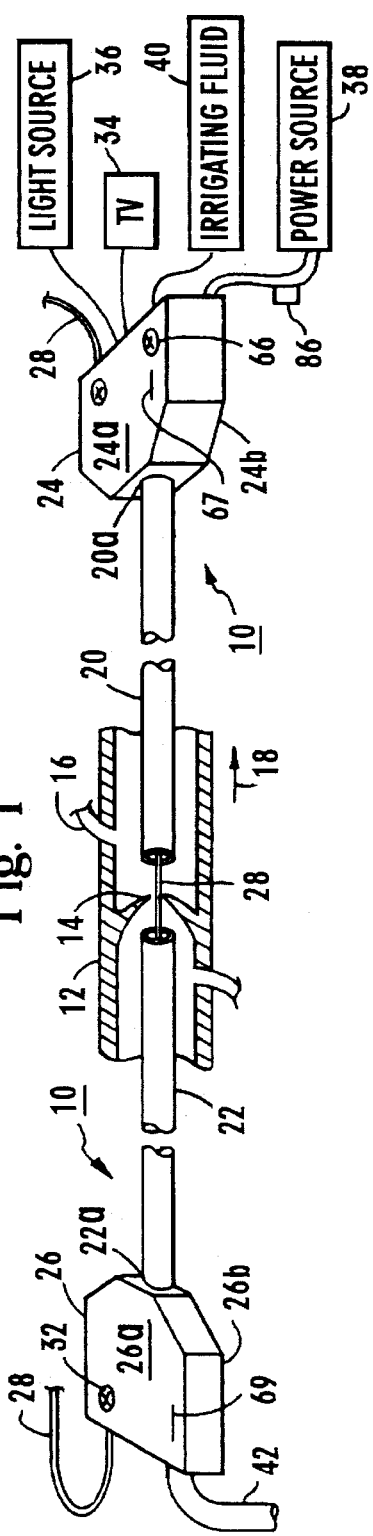
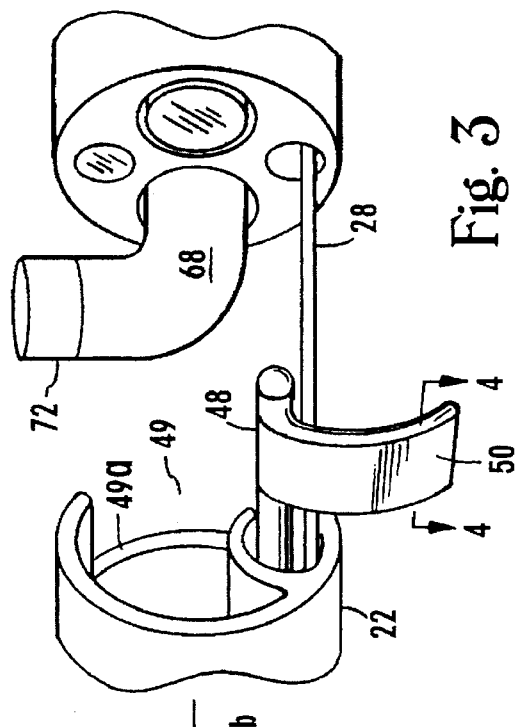
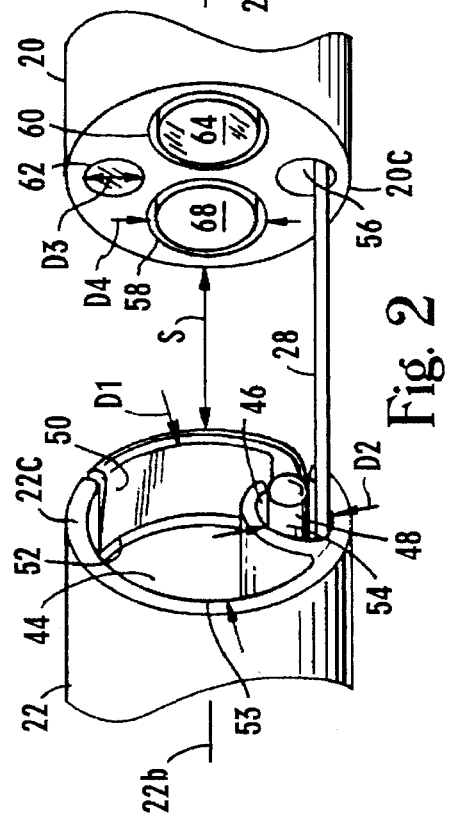
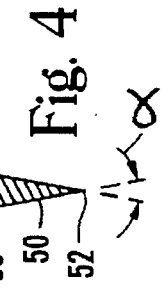

APPARATUS FOR IN SITU SAPHENOUS VEIN BYPASS AND LESS-INVASIVE VARICOSE VEIN TREATMENT

RELATED APPLICATIONS

This application is a continuation-in-part of U.S. patent application Ser. No. 08/183,994, filed Jan. 18, 1994, now U.S. Pat. No. 5,437,664, in the names of George Kick, Donald Cohen, and Derek Daw for an invention entitled "APPARATUS AND METHOD FOR VENOUS LIGATION", assigned to the same assignee as the present invention, from which this application claims priority and which is incorporated herein by reference. This application is also a continuation-in-part of U.S. patent application Ser. No. 08/315,074, filed Sep. 29, 1994, now abandoned in the names of George Kick, Donald Cohen, John Brustad, George Acosta, and Derek Daw for an invention entitled "IN SITU SAPHENOUS VEIN BYPASS APPARATUS WITH CAUTERIZING ELECTRODE", assigned to the same assignee as the present invention, from which this application claims priority and which is incorporated herein by reference.

FIELD OF THE INVENTION

The present invention relates generally to endoscopic surgical tools, and more particularly to endoscopic apparatus and methods for in situ saphenous vein bypass surgery and less invasive treatment of varicose veins.

BACKGROUND

Many hundreds of thousands of people each year experience partial or complete blockage of the femoral artery attributable to plaque build-up in the artery. When this occurs, the supply of oxygen-rich arterial blood to the leg is reduced, causing pain and, if it is left untreated, eventually leads to amputation of the leg.

For some blockages, it is possible to remove the blocking tissue by angioplasty or atherectomy, thereby preserving the functionality of the femoral artery. For more complex blockages, however, it is sometimes necessary to altogether bypass the blocked femoral artery. In other words, it is sometimes necessary to attach a substitute conduit to the femoral artery at a location that is upstream (proximal) to the blockage and a location that is downstream (distal) to the blockage, with the substitute conduit assuming the function of the femoral artery in delivering arterial blood to the leg. Such a bypass procedure may be required when the femoral artery has become too occluded or otherwise impaired between the upstream and downstream locations to transport the flow of blood required of it.

Frequently, the bypass conduit of choice is the patient's saphenous vein. The saphenous vein is the principle vein in the leg, and it is the vein that normally returns oxygen-depleted venous blood upwardly through the leg to the trunk of the body, for eventual transport of the blood to the heart and lungs for replenishing the blood with oxygen. It happens, however, that other veins exist in the leg which can duplicate the function of the saphenous vein. Consequently, it is feasible to modify the saphenous vein for use as a substitute for a blocked femoral artery.

To bypass the femoral artery using the saphenous vein, the saphenous vein is surgically severed in the upper leg, near the groin, and in the lower leg, near the ankle, to establish a bypass segment. Then, the bypass segment is attached ("anastomosed") to the femoral artery to bypass the blockage in the artery.

Unfortunately, the saphenous vein cannot simply be used as an artery without modification. First, this is because the saphenous vein, like all major veins but unlike major arteries, includes many openings into which venous blood flow from smaller, so-called "side branches", i.e., tributaries and perforators, can enter the main venous blood path back to the heart. The skilled artisan will appreciate that to prevent the unwanted flow of arterial blood directly into the venous system via the saphenous vein, the side branches and perforators must be ligated. Stated differently, by ligating the side branches, arterial blood which is to be permitted to flow through the saphenous vein and thereby bypass the occluded segment of the artery is prevented from invading the venous system through the side branches.

Typically, side branches are ligated by constricting the side branches with sutures. Unfortunately, ligating side branches with sutures can be time-consuming and labor-intensive, because all the side branches must be located either by making a large number of small incisions in the leg or by making one very large incision. Also, it is difficult to ligate side branches with sutures in less-invasive procedures, i.e., endoscopically. Nevertheless, to render the saphenous vein suitable for arterial use, the side branches must be blocked, i.e., ligated.

A second problem which must be addressed when using the saphenous vein to bypass the femoral artery is that the saphenous vein, like all major veins but unlike major arteries, contains one-way valves which ordinarily would permit the flow of blood only toward the heart (i.e., venous blood flow), not away from the heart (as is required for arterial blood flow). Thus, to render the saphenous vein suitable for arterial use, the one-way valve problem must be addressed.

One way to address the one-way valve problem is to reverse the entire saphenous vein bypass segment in a procedure referred to as the "reverse" procedure. In the reverse procedure, the segment of the saphenous vein which is to be used to bypass the femoral artery is removed from the leg, physically turned 180 degrees, and then replaced in the leg and anastomosed to the femoral artery. Thereby, the flow of arterial blood through the vein holds the valves open, instead of forcing them closed. Also, the side branches can be ligated when the saphenous vein has been removed from the leg, prior to repositioning the vein in the leg.

It will be appreciated that the reverse procedure requires making a lengthy incision in the leg to permit removal and repositioning of the saphenous vein. This is traumatic to the patient, and contributes to the length of the patient's hospital stay and recovery time.

Not surprisingly, a second method has been developed to address the one-way valve problem without requiring completely removing and then repositioning the saphenous vein. In this second method, referred to as "in situ bypass", the saphenous vein is left in place, and a cutting device known as a valvulotome is pushed or pulled through the saphenous vein to cut or otherwise disrupt the one-way valves, rendering them incompetent and thereby permitting arterial blood flow through the saphenous vein.

In situ bypass is not without its complications, however. The requirement remains that the side branches to the vein must be ligated. In the context of in situ bypass surgery, this typically requires making a number of small incisions or a single, long incision along the length of the vein to provide a surgeon access to the side branches to enable the surgeon to ligate the side branches. In either case, the trauma problems noted above that are associated with making a large number of incisions, or a single lengthy incision, remain.

Moreover, in situ bypass surgery, like many surgical procedures, can require that the surgical site be frequently irrigated to improve visualizing the site. This is particularly true when the procedure is performed endoscopically, i.e., when an optical fiber is advanced into the saphenous vein along with the valvulotome to provide the surgeon with an image of the operating site on a video monitor in the operating room. It is possible, however, that over-irrigation can cause ancillary damage to the leg or compromise the vessel itself.

As recognized by the present invention and disclosed in the above-referenced patent applications, side branches to the saphenous vein can be ligated less-invasively using electro-cautery. As further recognized by the present invention, the same less-invasive electro-ligation principles which apply to saphenous vein side branches can also apply to varicose veins. More particularly, the present invention recognizes that varicose veins can be treated by electro-ligation of the veins using less-invasive principles.

It is therefore an object of the present invention to provide a device for in situ saphenous vein bypass surgery that can less-invasively ligate side branches of a saphenous vein without requiring that excessive incisions be made in the patient's leg. Another object of the present invention is to provide an apparatus and method for less invasively bypassing a blocked femoral or distal artery. Still another object of the present invention is to provide an apparatus and method for in situ saphenous vein bypass surgery which is easy to use and cost-effective to manufacture.

SUMMARY OF THE INVENTION

A device for electro-ligation of a blood vessel includes a delivery catheter having a distal end and an optical image fiber positioned in the delivery catheter for generating an image of structure beyond the distal end of the delivery catheter. A hollow electrode which defines a cavity is disposed in the delivery catheter. In accordance with the present invention, the electrode is selectively advanceable beyond the distal end for cauterizing tissue. A temperature sensor is disposed in the cavity of the electrode for sensing the temperature thereof.

Preferably, the temperature sensor includes a thermocouple and two electrical wires attached to the thermocouple. Advantageously, an epoxy material is disposed in the cavity.

In one preferred embodiment, the delivery catheter is an operating catheter advanceable into a patient for cauterizing a side branch of a saphenous vein in situ. In this embodiment, the device further includes a flexible electrically conductive joining member, preferably a closed wound spring, which is connected to the electrode for transmitting electricity thereto. In an alternate embodiment, the delivery catheter is an endoscope, and the endoscope is advanceable into a varicose vein for cauterizing the varicose vein in situ.

For in situ saphenous vein bypass applications, a valvulotome can be operably associated with the electrode for cutting valves within the saphenous vein. As envisioned by the present invention, the valvulotome includes a fixed blade defining a fixed cutting edge and a movable blade defining a movable cutting edge facing the fixed blade. In accordance with principles discussed in detail below, the movable cutting edge has a closed position, wherein the blades are closely juxtaposed, and an open position, wherein the blades are spaced apart for receiving tissue therebetween.

Advantageously, the device of the present invention also includes a source of electricity electrically connected to the electrode and having a variable power output. A feedback device is electrically connected to the source of electricity. In the preferred embodiment, the feedback device includes a microprocessor and a sensor for sensing at least one parameter and generating a respective parameter signal in response thereto, and the microprocessor includes a comparator for receiving the parameter signal and comparing the parameter signal to a setpoint. In accordance with the present invention, the setpoint has a value that is dependent upon at least one of: electrical output parameters of the source of electricity, time rate of change of electrode temperature, and power output of the source of electricity. The comparator generates a control signal in response to cause the microprocessor to control the power output of the source of electricity.

In another aspect of the present invention, an apparatus for stopping blood flow through a blood vessel includes a delivery catheter having a distal end percutaneously positionable in the vessel. The apparatus also includes an electrode disposed in the delivery catheter and selectively advanceable beyond the distal end of the delivery catheter for facilitating electro-cautery of tissue to thereby stop blood flow from the tissue. Moreover, the apparatus includes a temperature sensor disposed in the electrode for generating a temperature signal representative of the temperature thereof, and a light transmitting member is disposed in the delivery catheter for generating an image of an object located beyond the distal end of the catheter for facilitating electro cautery.

In still another aspect of the present invention, a device for use in less-invasive surgery to inhibit blood flow through a blood vessel of a patient includes an electrode and a source of electricity electrically connected to the electrode. The source of electricity has a variable power output such that the source of electricity can be energized to energize the electrode to thereby cause the lumen of the blood vessel to collapse when the electrode is positioned in the vessel. A feedback device is electrically connected to the source of electricity, with the feedback device including a microprocessor and a sensor for sensing at least one parameter and generating a respective parameter signal in response thereto.

The microprocessor includes a comparator for receiving the parameter signal and comparing the parameter signal to a setpoint having a value dependent upon at least one of: electrical output parameters of the source of electricity, and power output of the source of electricity. As intended by the present invention, the comparator determines whether the parameter signal bears a first or second relationship to the setpoint, and the microprocessor causes the power output of the source of electricity to be decreased when the parameter signal bears the first relationship to the setpoint.

In yet another aspect, a method is disclosed for less-invasively stopping blood flow through a blood vessel in situ in a patient that includes making a percutaneous incision in the patient. Then, an electrode having a temperature sensor disposed therein is advanced into the vessel through the incision, and a temperature signal is generated that is representative of the temperature of the electrode. The electrode is then manipulated to cauterize tissue in the vessel while controlling energization of the electrode based upon the temperature signal.

The details of the present invention, both as to its construction and operation, can best be understood in reference to the accompanying drawings, in which like numerals refer to like parts, and which:

BRIEF DESCRIPTION OF THE DRAWINGS

FIG. 1 is a perspective view of the apparatus for in site saphenous vein bypass of the present invention, shown in one intended environment;

FIG. 2 is a perspective detail view of the operating ends of the control catheter and operating catheter, with the valvulotome and electrode in their housed positions, showing the cap in an exploded relationship with the control catheter;

FIG. 3 is a perspective detail view of the operating ends of the control catheter and operating catheter, with the valvulotome and electrode in their operating positions;

FIG. 4 is a cross-sectional view of the valvulotome as seen along the line 4—4 in FIG. 3;

DETAILED DESCRIPTION OF THE PREFERRED EMBODIMENT

Figure 5:
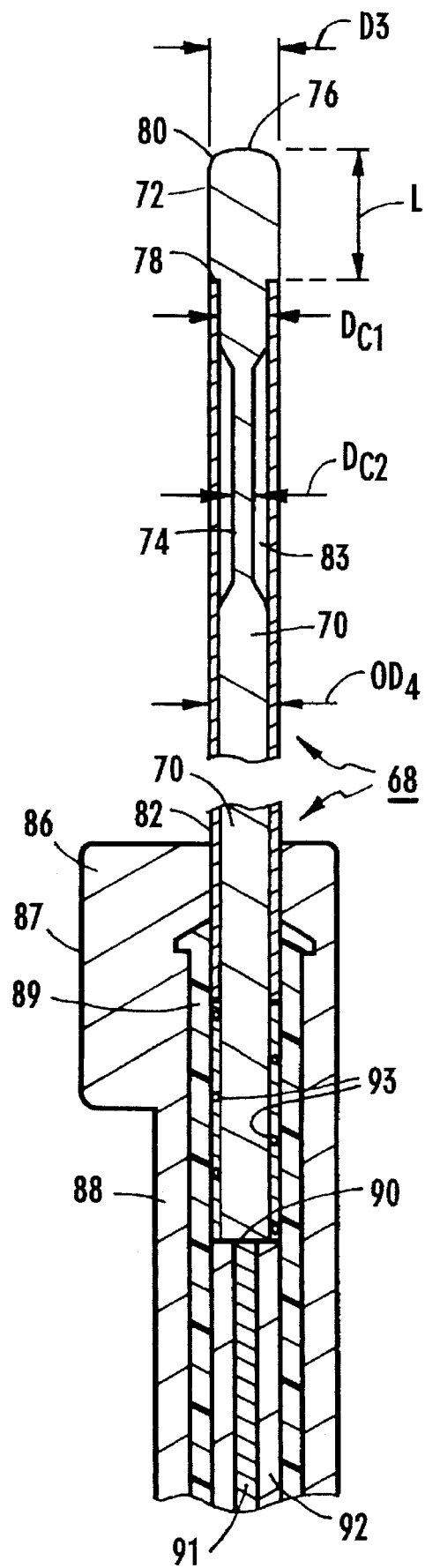
FIG. 5 is a cross-sectional view of the electrode as seen along the line 5—5 in FIG. 1.

Referring initially to FIG. 1, an apparatus is shown, generally designated 10, for in situ modification of a saphenous vein 12 for arterial use. As disclosed below, the apparatus 10 is used to modify the saphenous vein 12 by disrupting one-way valves 14 in the saphenous vein 12 and by electro-ligating side branches 16 to the saphenous vein 12. It is to be understood that the valves 14, until they are disrupted, permit only venous blood flow through the saphenous vein 12 and not arterial blood flow, i.e., undisrupted valves 14 permit blood flow through the saphenous vein 12 only toward the mink of the patient's body, in the direction indicated by the arrow 18, and prevent blood flow in the opposite direction.

As shown in FIG. 1, the apparatus 10 includes an operating catheter 20 and a control catheter 22. A first end 20a of the operating catheter 20 is connected to a flat working hub 24 having opposed first and second flat surfaces 24a, 24b, while a first end 22a of the control catheter 22 is connected to a flat cutting hub 26 having opposed first and second flat surfaces 26a, 26b. Preferably, both catheters have a 1:1 torque ratio; consequently, turning a hub 24, 26 a predetermined number of degrees (e.g., flipping the hub 24 180 degrees to reverse the position of the first side 24a and second side 24b) will cause the associated catheter 20, 22 to rotate the same number of degrees along its entire length.

A stainless steel guide wire 28 extends through both the catheters 20, 22 and the hubs 24, 26. The guide wire 28 has a diameter of approximately forty five hundredths of a millimeter (0.45 mm). Each hub 24, 26 includes a respective locking screw 30, 32 that can be manually tightened against the guide wire 28 to hold the guide wire 28 stationary relative to the hubs 24, 26 and catheters 20, 22.

FIG. 1 further shows that the working hub 24 is connected to a video monitor 34, e.g., a Sony video monitor, by an appropriate sterilizable camera coupler (not shown) of a type well known in the art. Preferably, the optical system including the camera coupler and video monitor includes a camera of the type well-known in the art having an auto-iris feature. If desired, the camera coupler can be housed within the working hub 24.

Moreover, the working hub 24 is connected to a light source 36, preferably a three hundred watt (300 w) Xenon light source of the type well-known in the art. Additionally, the working hub 24 is operably connected to a source 38 of electrical power by means more fully disclosed below. Preferably, the source 38 of electrical power is an electro-cautery power source suitable for supplying electricity for cauterizing tissue, such as the Bovie brand generator made by Valley Labs of Colorado. Also, a source 40 of irrigating fluid is connected to the working hub 24 for purposes to be shortly disclosed. FIG. 1 also shows that the cutting hub 26 is connected to a drain line 42.

Now referring to FIGS. 2 and 3, the control catheter 22 preferably is a biocompatible, flexible plastic tube, more preferably made of polyvinylchloride (PVC), and the catheter 22 defines a longitudinal axis 22b and an open second end 22c. A cap 43 can be positioned over the open second end 22c of the control catheter 22 for purposes to be disclosed below.

It can be appreciated in reference to FIGS. 2 and 3 that the control catheter 22 is formed by extrusion with a cylindrical drain lumen 44 and a cylindrical valvulotome lumen 46, both of which extend the length of the control catheter 22 into the cutting hub 26. It is to be understood that the drain lumen 44 is in fluid communication with the drain line 42 shown in FIG. 1. The diameter "D1" of the drain lumen 44 is preferably about one and eight tenths millimeters (1.8 mm), and the diameter "D2" of the valvulotome lumen 46 is preferably about two-tenths of a millimeter (0.2 mm). Thus, the outside diameter "OD1" of the control catheter 22 is between about two and one tenth millimeter (2.1 mm) and two and seven tenths millimeters (2.7 mm).

FIGS. 2 and 3 show that the guide wire 28 extends through the valvulotome lumen 46, and, when the locking screw 32 is not tightened against it, the guide wire 28 is slidably disposed in the control catheter 22. On the other hand, when the locking screw 32 is tightened, the guide wire 28 is held stationary in the control catheter 22. Alternatively, a third lumen (not shown) can be formed in the control catheter 22 for holding the guide wire 28 in lieu of the valvulotome lumen 46.

A stainless steel or rigid hard plastic valvulotome 48 is reciprocally disposed in the valvulotome lumen 46. As shown, the valvulotome 48 includes a cutting blade 50 that is formed with an interior cutting edge 52. Stated differently, the cutting edge 52 of the valvulotome 48 is oriented toward the control catheter 22. Preferably, the cutting edge 52 is sharpened by electro-discharge machining, and in brief reference to FIG. 4, the cutting blade 50 defines an angle α of about twenty (20) degrees, with the cutting edge 52 establishing the apex of the angle α.

As shown best in cross-reference to FIGS. 2 and 3, the valvulotome 48 is shaped as a partial cylinder. Also, the control catheter 22 is formed with a cut-out or recess 49 which is configured complementarily with the valvulotome 48. Consequently, when in a housed position shown in FIG.

2, the valvulotome 48 fits closely within the recess 49, i.e., the valvulotome 48 is flush with the control catheter 22 when the valvulotome 48 is in the housed position.

FIGS. 2 and 3 further show that the valvulotome 48 also includes a valvulotome shaft 54. It is to be understood that the valvulotome shaft 54 extends through the valvulotome lumen 46 of the control catheter 22, for manipulation of the valvulotome 48 by a surgeon. More particularly, the valvulotome 48 can be manipulated between the housed position shown in FIG. 2, wherein the valvulotome 48 presents an atraumatic aspect (i.e., is flush with the wall of the control catheter 22 as described above), and a cutting position shown in FIG. 3, wherein the valvulotome 48 can be manipulated to cut valves 14. To this end, the valvulotome shaft preferably has a torque ratio of 1:1.

Stated differently, in the housed position shown in FIG. 2, the cutting edge 52 of the valvulotome 48 faces a circumferentially-oriented wall 49a of the control catheter 22, to shield the cutting edge 52 from the saphenous vein 12. In this position, the only part of the valvulotome 48 which is exposed to the saphenous vein 12 is a non-sharp, preferably curvilinear outer edge 53.

On the other hand, in the cutting position (FIG. 3), the cutting edge 52 is distanced from the second end 22c of the control catheter 22, and the cutting blade 50 is mined radially outwardly away from the drain lumen 44. Thereby, the cutting edge 52 is exposed to the saphenous vein 12. It will be appreciated in reference to FIG. 3 that the valvulotome shaft 54 can be pulled relative to the control catheter 22 (i.e., moved to the left in FIG. 3) to move the cutting edge 52 against and into the valves 14 to thereby disrupt valves 14 in the saphenous vein 12.

FIGS. 2 and 3 show that the operating catheter 20 defines a longitudinal axis 20b which is generally coincidental with the axis 22b of the control catheter 22. Also, the operating catheter 20 is formed with a second end 20c, and the second end 20c of the operating catheter 20 is preferably closely spaced from the second end 22c of the control catheter 22. In the presently preferred embodiment, the second end 20c of the operating catheter 20 is spaced is distance "s" of about one centimeter (1 cm) from the second end 22c of the control catheter 22.

Like the control catheter 22, the operating catheter 20 preferably is a biocompatible, flexible plastic tube, more preferably made of polyvinylchloride (PVC). It can be appreciated in reference to FIGS. 2 and 3 that the operating catheter 20 is formed by extrusion with a cylindrical guide wire lumen 56, a cylindrical electrode lumen 58, and a cylindrical fiber lumen 60, all of which extend the length of the operating catheter 20 into the working hub 24. Also, a lumen is formed which closely holds a cylindrical illumination fiber 62.

It is to be understood that the guide wire lumen 56, electrode lumen 58, and fiber lumen 60 all terminate in the working hub 24 in standard Luer lock fittings, and each lumen 56, 58, 60 is in fluid communication with the source 40 of irrigating fluid (FIG. 1). In contrast, the illumination fiber 62 is connected to the light source 36.

The diameter "D3" of the illumination fiber 62 is preferably about six tenths of a millimeter (0.6 mm), and the diameter "D4" of the electrode lumen 58 is preferably about one and one-tenth of a millimeter (1.1 mm). The diameter of the guide wire lumen 56 is approximately equal to the diameter of the illumination fiber 62, and the diameter of the fiber lumen 60 is about equal to the diameter of the electrode lumen 58. The outside diameter "OD2" of the operating catheter 20 is between about two and one tenth millimeter (2.1 mm) and two and seven tenths millimeters (2.7 mm).

FIGS. 2 and 3 show that the guide wire 28 extends through the guide wire lumen 56 of the operating catheter 20 into the working hub 24 (FIG. 1), and, when the locking screw 30 is not tightened against it, the guide wire 28 is slidably disposed in the operating catheter 20. On the other hand, when the locking screw 30 is tightened, the guide wire 28 is held stationary in the operating catheter 20. Further, a light transmitting member, preferably an optical image fiber 64, is removably disposed in the fiber lumen 60. In accordance with principles well-known in the optical fiber art, the image fiber 64 includes a distal lens and the fiber 64 is connected to the camera coupling discussed previously, which in turn is connected to the video monitor 34.

After use, the image fiber 64 can be removed from the fiber lumen 60, the operating catheter 20 disposed of, and the image fiber 64 reused in another like operating catheter (not shown). In one presently preferred embodiment, the image fiber 64 is held in the fiber lumen 60 by at least one threaded fastener 66 (FIG. 1) which is threadably engaged with the working hub 24 and which can be tightened against the fiber 64 to hold the fiber 64 stationary within the operating catheter 20.

Referring to FIGS. 2 and 3, an electrode 68 is reciprocally disposed in the electrode lumen 58 and extends through the working hub 24, where it terminates in a standard banana plug connector for connection with the source 38 of electricity (FIG. 1). The electrode 68 can be moved between a housed position, shown in FIG. 2, wherein the electrode 68 is disposed substantially within the operating catheter 20, and an operating position, shown in FIG. 3, in which the electrode 68 extends beyond the second end 20c of the operating catheter 20 for exposing the electrode 68 to tissue.

As can be appreciated in reference to FIGS. 2 and 3, the electrode lumen 58 is offset from the axis 20b of the operating catheter 20. Likewise, the valvulotome lumen 46 is offset from the axis 22b of the control catheter 22. Recall that both catheters 20, 22 have 1:1 torque ratios, and that consequently the position of the valvulotome lumen 46 relative to the cutting hub 26 and the position of the electrode lumen 58 relative to the working hub 24 is constant. Accordingly, it will be appreciated that each flat hub 24, 26 can be marked or scored with indicators, e.g., lines 67, 69 shown in FIG. 1, to indicate the position of the electrode 68 or valvulotome 48, respectively.

FIG. 5 shows the details of the electrode 68. As shown, the electrode 68 includes an elongated electrical conductor 70 having a cylindrically-shaped electrode tip 72 formed integrally on the distal end of the conductor 70. Preferably, the conductor 70 has an electrical resistance below ten ohms per foot (10 $\Omega$/ft). In the preferred embodiment, the conductor 70 with electrode tip 72 is made of type 304 stainless steel. By manufacturing the electrode tip 72 integrally with the conductor 70, manufacturing costs of the electrode 68 are minimized, and a firm connection is established between the electrode tip 72 and the conductor 70.

FIG. 5 also shows that the conductor 70 has an outside diameter $D_{C1}$ of about between about sixteen thousandths of an inch and eighteen thousandths of an inch (0.016"–0.018"). Also, the conductor 70 tapers radially inwardly to a bendable segment 74 having a diameter $D_{C2}$ of about five thousandths of an inch (0.005"). As the skilled artisan will appreciate, the bendable segment 74 is malleable and flexible. Consequently, the segment 74 can be bent into a predetermined curvilinear shape to facilitate advancing the electrode 68 into a side branch 16 for electro cautery thereof.

As shown best in FIG. 5, the electrode tip 72 is formed with a rounded distal end 76. An abutment surface 78 is established by the electrode tip 72, and the abutment surface 78 radially projects beyond the conductor 70. Preferably, the electrode tip 72 has a diameter $D_3$ of between about twenty eight thousandths of an inch and ninety two thousandths of an inch (0.028"–0.092"), and more preferably the diameter $D_3$ is about seven-tenths of a millimeter (0.7 mm), i.e., about twenty eight thousandths of an inch (0.028").

The length L of the electrode tip 72 is between about one to ten millimeters (1–10 mm). Specifically, the length L is established to be approximately equal to the maximum expected diameter of the side branch into which the electrode 68 is advanced.

In the presently preferred embodiment, a non-sticking, non-insulative substance 80 is deposited on the surface of the electrode tip 72 to inhibit sticking of the electrode tip 72 to body tissue during energization of the electrode tip 72. Preferably, the substance 80 is chrome which is deposited on the electrode tip 72 by vapor deposition. Alternatively, the electrode tip 72 can be coated with titanium nitride.

FIG. 5 also shows that an insulative sheath 82 surrounds the conductor 70 and abuts the abutment surface 78 of the electrode tip 72. As can be seen in FIG. 5, the outer surface of the sheath 82 is flush with the outer surface of the electrode tip 72, and an air space 83 is established between the sheath 82 and the bendable segment 74. In accordance with the present invention, the sheath 82 is bonded to the conductor 70 with a high-temperature epoxy.

As intended by the present invention, the sheath 82 is made of an electrically resistive, smooth, biocompatible material, such as PEBAX® made by Atochem, Inc. of New Jersey, or TFE Teflon®, which typically has a dielectric strength of about seven hundred to one thousand volts per mil of material (700–1000 v/mil). Also, the sheath 82 is made of a material which will not easily melt or breakdown under the high temperatures that are typically generated during electro cautery. Further, the sheath 82 should be made of a material that has a low coefficient of friction.

PEBAX® is the presently preferred material of choice for the sheath 82 in light of its above-mentioned attributes and because it is relatively flexible, elastic, and has a low coefficient of friction. These attributes permit the sheath 82 to be easily advanced through a potentially curvilinear, small-diameter lumen of blood vein or an endoscopic instrument. Further to this end, the outside diameter $OD_4$ of the sheath 82 (and, hence, the outside diameter of the electrode 68) is preferably equal to less than about one millimeter (1 mm). In one presently preferred embodiment, the outside diameter $OD_4$ of the sheath 82 is between about twenty eight thousandths of an inch and ninety two thousandths of an inch (0.028"–0.092"). Alternative materials which can be used for the sheath 82 include polyimide, polyethylene, and polypropylene.

If desired, a sensor 84 (FIG. 3) can be attached to the electrode tip 72. The sensor 84 can be a thermocouple, thermistor, or other suitable temperature-sensing device. Alternatively, the sensor 84 can be a pressure sensor for sensing fluid pressure at the distal end of the electrode 68.

FIG. 5 shows that a flat, generally paralellepiped-shaped bend indicator 86 is bonded to the sheath 82 outside the operating catheter 20 shown in FIGS. 2 and 3, i.e., proximal to the first end 20a of the operating catheter 20. As shown, the indicator 86 is formed with a projecting edge 87 that is distanced from the sheath 82. As intended by the present invention, the bend indicator 86 is oriented during manufacturing such that the projecting edge 87 extends outwardly in the same direction as the bend of the bendable segment 74 of the conductor 70. The indicator 87 remains outside the patient's body during surgery, and the operator of the electrode 68 can consequently ascertain during surgery the direction in which the bendable segment 74 of the conductor 70 has been bent.

FIG. 5 shows that the bend indicator 86 is formed integrally with a metal jacket 88, and the jacket 88 surrounds the sheath 82 to transmit torque to the electrode 68. An insert 89 made of silicone rubber is disposed between the jacket 88 and sheath 82. Further, the electrode 68 has a proximal end 90, and a high voltage line, including a high voltage lead 91 and high voltage insulator 92, abuts the proximal end 90 of the electrode 68. A wire 93 is soldered to the high voltage lead 91 and conductor 70 to further ensure electrical contact between the two components. It is to be appreciated that the high voltage lead 91 in turn is electrically connected to the source 38 of electricity (FIG. 1).

Figure 6:
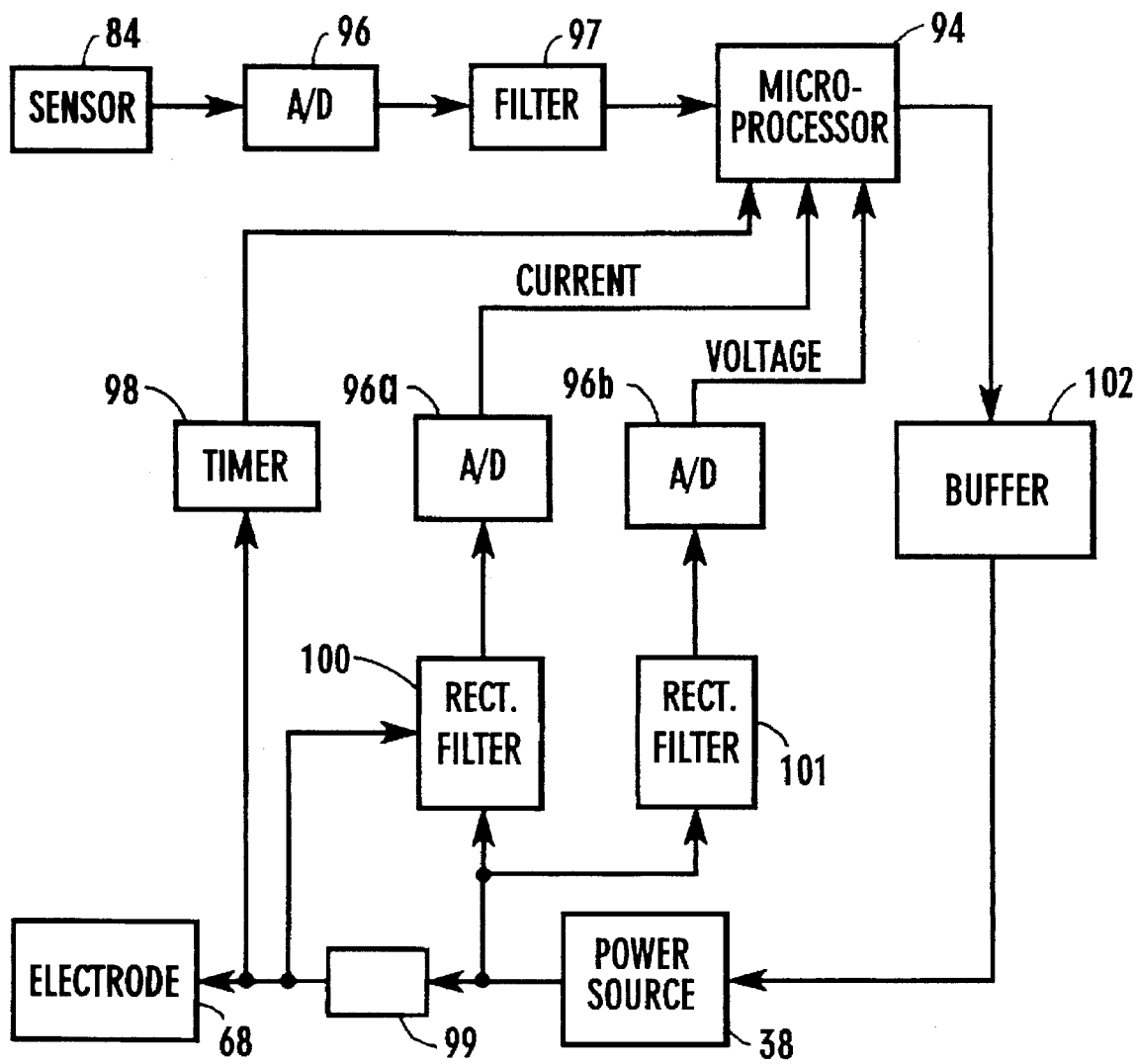
FIG. 6 is a block diagram of the electrical components associated with the electrode.

Reference is now made to FIGS. 5 and 6. The electrode 68 is electrically connected to the source 38 of electricity. It is to be appreciated that both the sensor 84 and electrode tip 72 of the electrode 68 are electrically connected to the source 38 of electricity.

As intended by the present invention, the electrode 68 is selectively energized by the source 38 of electricity to stop blood flow from side branches and other tissue within the saphenous vein. To this end, the source 38 of electricity is electrically connected to a microprocessor 94 which is advantageously a type "486" microprocessor. Alternatively, an equivalent programmed chip can be used in lieu of the microprocessor 94.

As disclosed more fully below, the microprocessor 94 is electrically connected to the source 38, and the microprocessor 94 generates a control signal for controlling the source 38 in response to, inter alia, signals from the sensor 84. If desired, indicators 95 (FIG. 1) can be provided for displaying electrode 68 voltage, current, impedance, temperature, and other parameters, in accordance with the operation of the electrode 68 disclosed below.

Particularly referring to FIG. 6, the sensor 84 is connected to an analog-to-digital ("A/D") converter 96, for converting the analog temperature signal from the sensor 84 into a digitized signal. The A/D converter 96 can advantageously be a type AD57804P converter made by Burr Brown, or some other suitable converter known in the art.

FIG. 6 further shows that the A/D converter 96 is connected to a noise filter 97. The noise filter 97 can be a hardware or, more preferably, software filter which filters noise from the digitized signal from the sensor 84. For example, the filter 97 can be programmed to discriminate against five hundred kilohertz (500 KHz), sixty Hertz (60 Hz) or fifty Hertz (50 Hz) noise from nearby electrical components. The filter 97 can also be programmed to average a predetermined number (e.g., ten) of consecutive signals from the sensor 84 and output a signal representative of the average, or the filter 97 can be a low-pass filter. When the noise filter 97 is a software filter, it can function by averaging a plurality of (e.g., ten) sensor signals in accordance with means well-known in the art.

Also, the filter 97 can be programmed to block a signal from the sensor 84 which greatly varies from the immediately previous signal. A great variance from one signal to the next may indicate an erroneous or spurious signal level. In other words, if a first signal from the sensor indicates an electrode tip 72 temperature of, e.g., eighty degrees centigrade (80° C.), and a second signal that is immediately temporally after the first indicates an electrode tip 72 temperature which varies by more than a predetermined mount (e.g., 10° C.) from the first signal, the filter 97 blocks the second signal from further processing. The hardware components, if any, of both the A/D converter 96 and the noise filter 97 can be housed in the electrode 68 or source 38. When the filter 97 is a software filter, the software filter 97 can be part of the microprocessor 94.

FIG. 6 also shows that a timer 98 is provided which monitors the length of time the source 38 energizes the electrode tip 72. The timer 98 generates a signal representative of the length of time of electrode tip 72 energization and sends this signal to the microprocessor 94. When the length of time exceeds a predetermined time period, e.g., a time period between about ten seconds and forty seconds (10 sec–40 sec), the microprocessor 94 causes the source 38 to stop energizing the electrode tip 72.

Additionally, components are provided for measuring the output voltage and current of the source 38 of electricity, and for providing signals representative of the output voltage, current, power, and impedance (and, hence, the voltage, current, power, and tissue impedance at the tip of the electrode tip 72) to the microprocessor 94. More specifically, a component 99, e.g., a current sensing transformer or resistor, is connected in series between the source 38 of electricity and the electrode tip 72, and a current rectifier filter ("R/F") 100 samples the voltage upstream and downstream of the component 99. Accordingly, the current R/F 100 outputs a signal representative of the output current of the source 38 of electricity.

Also, a voltage sampling R/F 101 is provided for generating a signal representative of the output voltage of the source 38 of electricity. Advantageously, both the current and voltage R/Fs 100, 101 can be full wave diode rectifiers with associated filtering capacitors connected in a configuration well-known in the art.

FIG. 6 shows that the current and voltage R/Fs 100, 101 are respectively connected to A/D converters 96a, 96b, each of which is substantially similar to the temperature A/D converter 96. In turn, both A/D converters 96a, 96b are connected to the microprocessor 94.

Still referring to FIG. 6, the microprocessor 94 generates an output control signal and sends the control signal to an electrical buffer 102. The buffer 102 is any suitable device which essentially isolates the microprocessor 94 from the source 38 of electricity, and which provides correct driving signals to the source 38.

The output signal from the buffer 102 is sent to the source 38 of electricity to control the output power of the source 38 of electricity. To do this, the control signal can be used to vary the output voltage of the source 38 of electricity, or the modulation of the signal from the source 38 of electricity, by means well-known in the art. For example, the signal from the buffer 102 can be used as the bias signal to a power transistor (not shown) that is part of the output circuitry of the source 38 of electricity. Consequently, as the signal from the buffer 102 changes, the bias of the transistor changes to change the output of the source 38 of electricity.

Figure 7:
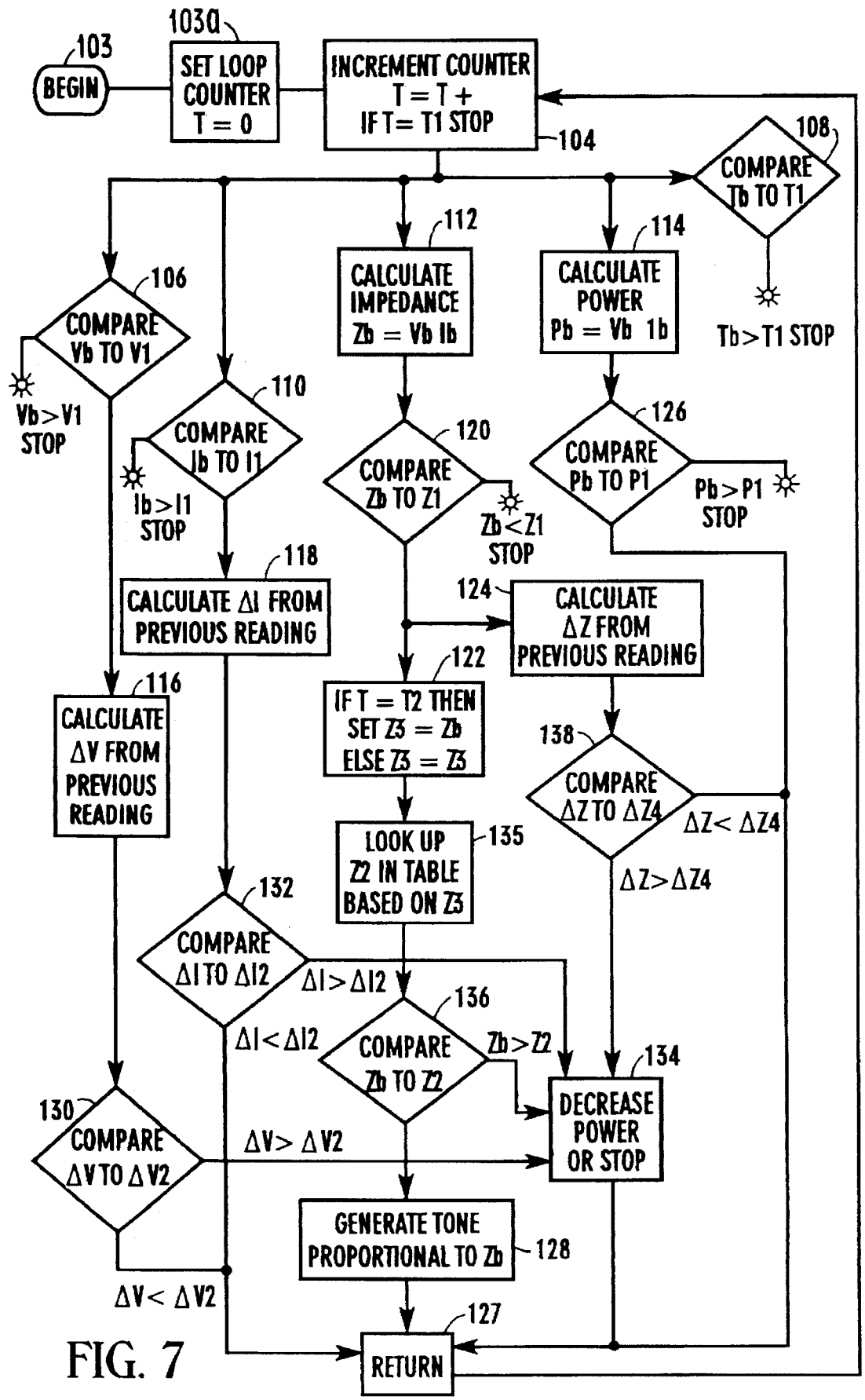
FIG. 7 is a flow chart of the microprocessor logic for generating the control signal for the electrode.

Now referring to FIG. 7, the details of the operation of the microprocessor 94 can be seen. The microprocessor 94 commences a sampling cycle at begin circle 103. From the circle 103, the microprocessor proceeds to block 103a, wherein a software counter "T" is set equal to zero. Then at block 104, "T" is set equal to T+1. If, at block 104, T equals a predetermined software counter "$T_1$", the microprocessor 94 stops, i.e., exits the routine shown in FIG. 7.

Otherwise, the microprocessor 94 proceeds in parallel to decision blocks 106, 108, and 110, and to blocks 112 and 114. At decision blocks 106, 108, 110, the microprocessor 94 retrieves from memory and then respectively compares source 38 of electricity output voltage ($V_b$), electrode tip 72 temperature ($T_b$), and source 38 of electricity output current ($I_b$) to respective predetermined voltage, temperature, and current setpoints V1, T1, I1. As more fully disclosed below, the setpoints V1, T1, I1, like the other setpoints disclosed herein with respect to impedance, may be variably patient-dependent, power-dependent, or temperature-dependent, in that the respective values of the setpoints may be established depending upon the characteristics of the patient as indicated by the output parameters of the source 38 of electricity, or by the power setting of the source 38, or by the temperature indicated by the sensor 84. If either $V_b$ or Tb exceeds its predetermined setpoint, or if $I_b$ falls below its predetermined setpoint, the microprocessor 94 generates a control signal to cause the source 38 of electricity to stop energizing the electrode tip 72. Otherwise, the microprocessor 94 proceeds to blocks 116, 118.

At block 112, on the other hand, the microprocessor 94 calculates the impedance ($Z_b$) of the tissue adjacent the electrode tip 72 by dividing $V_b$ by $I_b$. Then, the microprocessor 94 moves to decision block 120, where the microprocessor 94 compares $Z_b$ to a predetermined setpoint impedance Z1. If $Z_b$ exceeds Z1, poor electrical connection or poor placement of the electrode tip 72 may be indicated. In such a case, the microprocessor 94 generates a control signal to cause the source 38 of electricity to stop energizing the electrode tip 72. As intended by the present invention, the source 38 of electricity is deenergized before $Z_b$ reaches zero (0). Else, the microprocessor 94 proceeds to blocks 122 and 124. In the presently preferred embodiment, Z1 is set equal to about fifty ohms.

It is to be understood that while overall impedance is used in the presently preferred embodiment, the phase difference between $V_b$ and $I_b$ can be measured for determining the capacitive impedance component and resistive impedance component, and then either impedance component can be used in lieu of or in addition to $Z_b$. Indeed, the phase difference between $V_b$ and $I_b$ can be used as an input to the microprocessor 94 in lieu of or in addition to the parameters discussed above.

Likewise, at block 114, the microprocessor 94 calculates the output power ($P_b$) of the source 38 of electricity by multiplying $V_b$ and $I_b$. Then, the microprocessor 94 moves to decision block 126, where the microprocessor 94 compares $P_b$ to a predetermined setpoint power P1. If $P_b$ exceeds P1, the microprocessor 94 generates a control signal to cause the source 38 of electricity to stop energizing the electrode tip 72. Otherwise, the microprocessor 94 proceeds to return block 127, and thence back to block 104.

At blocks 116 and 118, the microprocessor 94 respectively calculates the difference between $V_b$, $I_b$, and $V_{b-1}$, $I_{b-1}$ to yield $\Delta V$, $\Delta I$, where $V_{b-1}$, $I_{b-1}$, are the respective voltage and current values calculated in the immediately preceding cycle. Alternatively, $V_{b-1}$, $I_{b-1}$ can be averages of the n preceding corresponding values where n=any integer, e.g., ten (10), three (3), etc.

From blocks 116, 118, the microprocessor 94 moves to respective decision blocks 130, 132. At block 130, the microprocessor 94 compares $\Delta V$ to a predetermined voltage difference, i.e., $\Delta V_2$. If $\Delta V$ exceeds $\Delta V_2$, the microprocessor 94 moves to block 134, wherein the microprocessor 94 generates a control signal to cause the source 38 of electricity to deactivate or to reduce its power output by a predetermined increment ΔP, e.g., by two to four watts (2 w–4 w). Otherwise, the microprocessor 94 moves to block 127 and thence back to block 104 for another cycle.

Likewise, at block 132, the microprocessor 94 compares ΔI to a predetermined current difference, i.e., $ΔI_2$. If ΔI exceeds $ΔI_2$, the microprocessor 94 moves to block 134, wherein the microprocessor 94 generates a control signal to cause the source 38 of electricity to reduce its power output by ΔP. Otherwise, the microprocessor 94 moves to block 127 and thence to block 104 for another cycle.

Recall that at block 120 the microprocessor 94 compared $Z_b$ to a predetermined constant impedance setpoint Z1. As shown in FIG. 7 starting at block 122, the microprocessor 94 also compares $Z_b$ to a variable impedance setpoint Z2 which is patient-dependent.

More specifically, at block 122 the microprocessor 94 sets an entering argument variable Z3 equal to $Z_b$ if T equals a predetermined stabilization time period T2. Otherwise, the entering argument variable Z3 is set equal to itself. More specifically, when T<T2, Z3 is set equal to a relatively low default value. When T=T2, Z3 is set equal to $Z_b$, and when T>T2, Z3 remains equal to the value of $Z_b$ set at T=T2. Thus, the entering argument Z3 is patient-dependent. Alternatively, the entering argument Z3 can depend on the power setting of the source 38 of electricity, or on the temperature signal from the sensor 84. In the preferred embodiment, T2 equals between about two (2) seconds to ten (10) seconds, and the default value of Z3 is equal to about two hundred ohms (200 Ω).

Then, the microprocessor 94 moves to block 135, wherein the microprocessor 94 retrieves a predetermined impedance limit Z2 by accessing a data table and using Z3 as the entering argument. A representative table is provided herein as Table 1. From block 135, the microprocessor 94 moves to decision block 136, wherein $Z_b$ is compared to Z2. If $Z_b$ exceeds Z2, the microprocessor 94 moves to block 134 to reduce source 38 of electricity output power or deenergize the electrode tip 72 altogether, and thence to block 128 to generate a tone representative of $Z_b$. Otherwise, the microprocessor 94 moves directly to block 128 to generate a tone representative of $Z_b$. It is to be understood that while block 128 in FIG. 7 indicates that a tone representative of impedance is generated, the tone or other tones could be generated which are representative of the other parameters discussed herein. From block 128, the microprocessor 94 moves to block 127 and then returns to block 104.

The skilled artisan will appreciate that the operation of the microprocessor 94 at block 122 ensures that the entering argument variable Z3 is set equal to a relatively stabilized $Z_b$. More particularly, for a brief initial stabilization period (T2), power interruption is avoided when minor transients in impedance ($Z_b$) might occur and otherwise cause the microprocessor 94 to deenergize the source 38 of electricity. Stated differently, the microprocessor 94 reduces source 38 output power during the stabilization time T2 only in the instance when $Z_b$ is less than the initial default value of Z2, which is accordingly set equal to a relatively low (e.g., eight hundred ohms (800 Ω) value.

On the other hand, after the stabilization period T2 elapses, $Z_b$ can be expected to reach a steady state value while the tissue surrounding the electrode 68 is treated by the electrode 36. During this treatment period, the entering argument Z3 is defined to be equal to the value of $Z_b$ at time T=T2, and the table look-up of Z2 is thus accomplished using a patient-dependent entering argument Z3.

From block 124, the microprocessor 94 proceeds to decision block 138, wherein the microprocessor 94 compares ΔZ to a predetermined impedance difference, i.e., ΔZ4. If ΔZ exceeds ΔZ4, the microprocessor 94 moves to block 134, wherein the microprocessor 94 generates a control signal to cause the source 38 of electricity to reduce its power output by ΔP, and thence to block 127. Otherwise, the microprocessor 94 moves directly to block 127, and thence to block 104 for another cycle.

Thus, at blocks 130, 132, 134 the microprocessor 94 determines whether the time rate of change of $V_b$, $I_b$, or $Z_b$ are excessive, and, if so, the microprocessor 94 reduces the output power of the source 38 of electricity, or deenergizes the electrode tip 72 altogether. The present invention also envisions calculating the time rate of change of temperature $T_b$ in a like manner and reducing the output power of the source 38 of electricity in response to an excessively rapid increase in $T_b$ or in the time rate of change of $T_b$, as more fully disclosed below in reference to FIG. 9.

The present invention contemplates the above-disclosed operation of the microprocessor 94 because, as recognized by the present invention, the tissue impedance at the tip of the electrode tip 72, and the temperature of the tip of the electrode tip 72, is affected by the characteristics of the tissue immediately adjacent the electrode tip 72.

More particularly, when the tissue has not yet been cauterized, the impedance at the electrode tip 72 tip is relatively low. In contrast, when the tissue has just undergone cauterization, the impedance at the electrode tip 72 tip is relatively high. Thus, the output voltage, current, and impedance of the source 38 of electricity are all affected by the cauterization of tissue adjacent the electrode tip 72. Stated differently, the magnitudes of the output voltage and current of the source 38 of electricity, and the magnitude of the impedance of the tissue adjacent the electrode tip 72, are dependent upon the body characteristics of the patient. Likewise, the temperature ($T_b$) of the electrode tip 72 tip also depends in part upon the characteristics of the tissue adjacent the tip of the electrode tip 72.

Hence, by automatically controlling (e.g., raising or lowering) the output of the source 38 of electricity based upon any one of or a combination of $Z_b$, $I_b$, $V_b$, $P_b$, and $T_b$ (and their respective time derivatives and resistance quotients), the present invention ensures that tissue adjacent the venous wall is not damaged any further than necessary to effect cauterization. Also, by precisely controlling the output of the source 38 of electricity, the present invention ensures that tissue is precisely cauterized as appropriate for side branch 16 closure. Alternatively, by automatically generating a tone representative of any one of or a combination of $Z_b$, $I_b$, $V_b$, $P_b$, and $T_b$ and their respective time derivatives, the present invention enables the surgeon to precisely control the source 38.

It is to be further understood that the present invention contemplates establishing power dependent predetermined setpoints, i.e., setpoints that vary with the manually-established power setting of the source 38 of electricity. Thus, V1, I1, Z1, Z2, Z3, P1, T1, and ΔZ4 can all vary with the power setting of the source 38 of electricity. In such an embodiment, a data table correlating power setting with predetermined setpoints is stored in the electronic memory of the microprocessor 94 for look-up by the microprocessor 94 at the appropriate decision blocks discussed above.

The disclosure above refers to an embodiment wherein the power output of the source 38 of electricity is established in response to, among other things, tissue impedance.

However, the present invention also contemplates other means for establishing the power output of the source 38. For example, the power output of the source 38 of electricity can be keyed to time, or to tissue temperature as measured by the sensor 84.

More particularly, the source 38 can initially output "P" watts for a predetermined time period, e.g., one second, and then step decreased to 0.75 P watts. After another predetermined time period, e.g., two seconds, the power output can be step decreased to 0.5 P watts and held at 0.5 P watts for yet another predetermined time period, e.g., seventeen seconds. Then, the source 38 can be deenergized after a total energization time of twenty seconds. The total energization time may be as low as six seconds, however.

Alternatively, the source 38 can initially output "P" watts until a predetermined tissue temperature, e.g., one hundred twenty degrees Fahrenheit (120° F.), has been reached, and then step decreased to 0.75 P watts. After another predetermined temperature, e.g., one hundred fifty degrees Fahrenheit (150° F.), has been reached, the power output can be step decreased to 0.5 P watts and held at 0.5 P watts until yet another predetermined temperature, e.g., one hundred eighty degrees Fahrenheit (180° F.), has been reached, at which point the source 38 is deenergized.

It is to be understood that during either of the above-disclosed operations, energization of the source 38 of electricity can be decreased or stopped immediately in response to any one or more of the previously discussed parameters (temperature, impedance, voltage, current, phase, and time rates of change thereof) reaching a respective predetermined safety shut-off setpoint. Furthermore, in the event that one of the safety shut-off setpoints is reached relatively quickly, e.g., within six seconds of initial source 38 energization, the initial power output "P" can be decreased by a predetermined amount, e.g., one watt, and then the cycle recommended. Moreover, if the safety shut-off setpoint for a particular parameter, e.g., impedance, is reached, but the value of the parameter unexpectedly 38 of electricity can nonetheless be decreased or stopped.

In the overall operation of the apparatus 10, reference is made to FIGS. 1–3. A first small incision is made in the saphenous vein 12 in the lower leg of the patient, near the ankle or calf. Also, a second small incision is made in the saphenous vein 12 in the upper leg or groin of the patient.

The cap 43 is positioned over the second end 22c of the control catheter 22, and the capped second end 22c is then advanced into the first incision, through the saphenous vein 12, and out of the second incision. Then, the cap 43 is removed and the guide wire 28 is advanced through the guide wire lumen 46 of the control catheter 22 from the first end 22a through the second end 22c, and into and through the guide wire lumen 56 of the operating catheter 20. The catheters 20, 22 are positioned on the guide wire as appropriate to establish the distance "s" between the second ends 20c, 22c of the catheters 20, 22, and the locking screws 30, 32 on the hubs 24, 26 are then tightened to prevent further relative motion between the catheters 20, 22. It will be appreciated that with this combination of structure, the image fiber 64 transmits an image of objects located between the second ends 20c, 22c of the catheters 20, 22 for display on the video monitor 34.

Next, both catheters are advanced into the saphenous vein 12 with the electrode 68 and valvulotome 48 in the housed positions shown in FIG. 2. The catheters are so advanced until the second end 20c of the operating catheter 20 is positioned on a proximal side of a valve 14 and the second end 22c of the control catheter 22 is positioned on the distal side of the valve 14.

The valvulotome 48 is then advanced through the valve 14 to the cutting position shown in FIG. 3. It will be appreciated that when the valvulotome 48 is advanced through the valve 14 to the proximal side thereof, the optical fiber 64 transmits an image of the valvulotome 48 and the valve 14 about to be disrupted. To disrupt the valve 14, the valvulotome 48 is pulled back distally into the valve 14. After valve disruption, the valvulotome 48 is moved to the housed configuration shown in FIG. 2 to present an atraumatic aspect, and the catheters 20, 22 are advanced together through the saphenous vein 12 to sequentially disrupt the valves 14.

Also, when the surgeon visualizes, on the monitor 34, side branches 16 requiring ligation or bleeding valve 14 tissue requiring cauterization, the electrode tip 72 of the electrode 68 is selectively advanced out of the electrode lumen 58 to the operating position shown in FIG. 3, and into the side branch 16 sought to be ligated or against the tissue sought to be cauterized. Next, the source 38 of electricity activated to electro-ligate the side branch. The electrode 68 is then retracted into the operating catheter 20. In the preferred embodiment the electrode 68 is manually moved to the operating position by, e.g., urging against the bend indicator 86.

Periodically, it may be desirable to irrigate the lumens 56, 58, 60 of the operating catheter 20, to prevent blood from clotting therein and to improve visualization of the space between the second ends 20c, 22c of the catheters 20, 22. Accordingly, irrigating fluid from the source 40 of fluid is flushed through the lumens 56, 58, 60. Excess irrigating fluid is then drained by gravity through the drain lumen 44 of the control catheter 22, thereby alleviating potentially deleterious fluid build-up in the patient's leg.

It is to be understood that while the electrode 68 disclosed above is a monopolar device, it may also be a bi-polar device, e.g., the electrode 68 can have electrodes configured like those disclosed in co-pending U.S. patent application Ser. No. 08/054,123, filed Apr. 26, 1993, for an invention entitled "Bi-Polar Electrocauterizer", now abandoned, assigned to the sole owner of the present invention and incorporated herein by reference.

It is to be further understood that the valves within the saphenous vein may be disrupted with other valvulotomes (not shown) prior to using the present invention. In such a case, the control catheter 22 can be omitted, and the operating catheter 24 advanced over the guide wire 28 proximally to distally through the saphenous vein to ligate side branches as disclosed. Or, the control catheter 22 can be included for drainage purposes, with the valvulotome 48 omitted.

Figure 8:
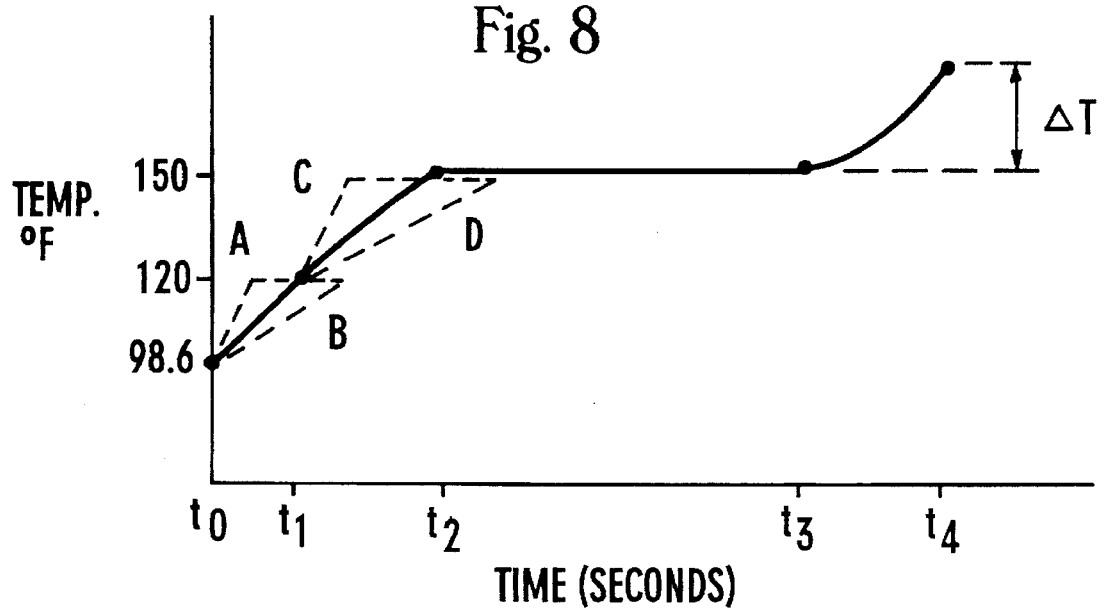
FIG. 8 is a graph of the preferred temperature profile versus time for blood vein electro-coagulation.
Figure 9:
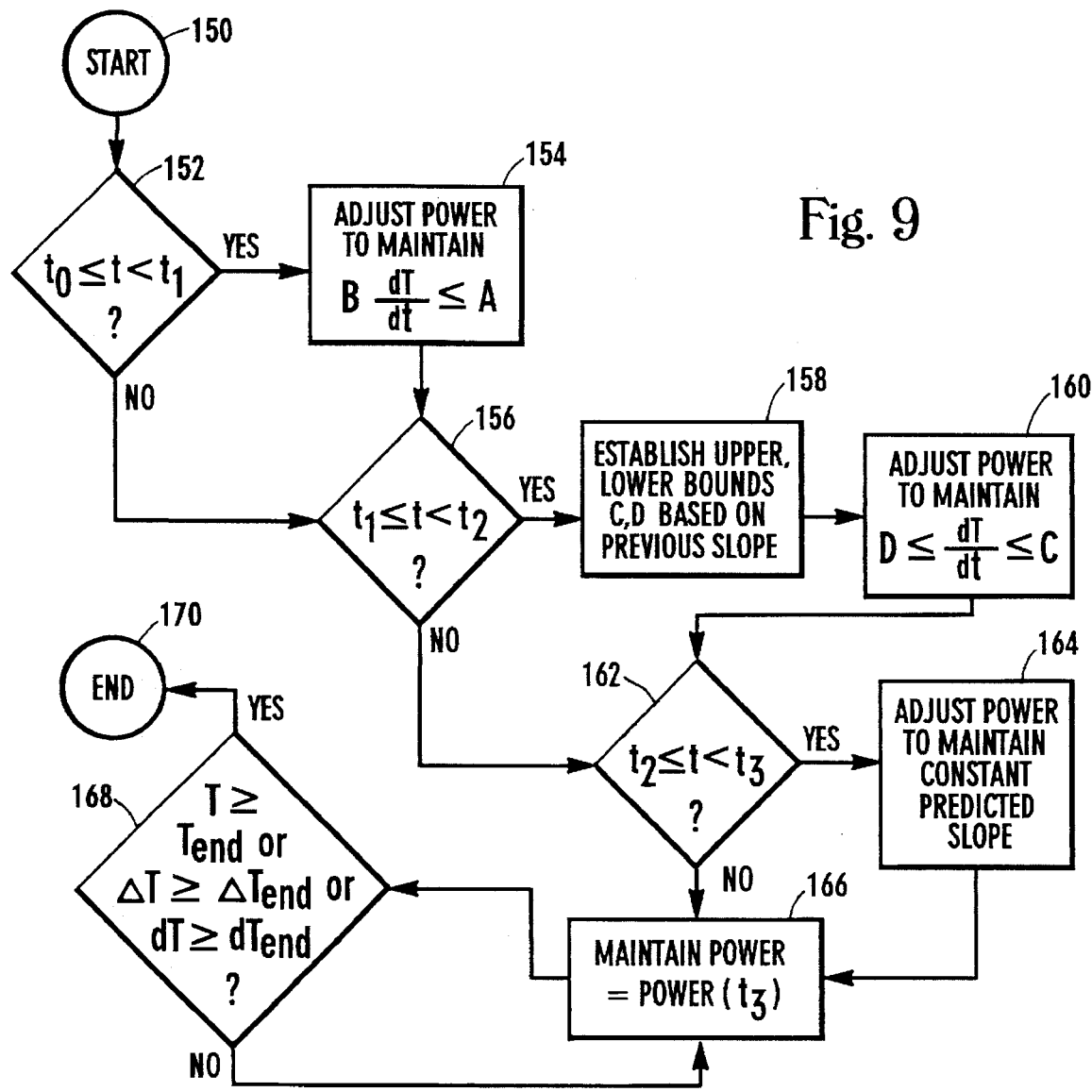
FIG. 9 is a flow chart of the microprocessor logic for establishing the temperature profile shown in FIG. 8.

In reference to FIGS. 8 and 9, one particularly preferred embodiment of controlling the power output of the source 38 of electricity in response to the time rate of change of electrode 68 temperature can be understood. More specifically, FIG. 8 shows a desired time-dependent temperature profile for electrocautery of tissue within a blood vessel, and FIG. 9 shows the steps implemented by the microprocessor 94 for establishing the desired time-dependent temperature profile.

As shown in FIG. 8, the desired temperature profile is characterized by four intervals. The first interval commences at an initial time $t_0$ and an electrode temperature of 98.6° F. and ends at a first time $t_1$, e.g., two seconds. The first time $t_1$ corresponds approximately to an electrode temperature of 120° F. Additionally, the second interval commences at the first time $t_1$ and ends at a second time $t_1$, e.g., four seconds, corresponding to an electrode temperature of approximately 150° F. Thus, the length of the second interval, in the exemplary embodiment shown, is two seconds.

Further, the third interval commences at the second time $t_2$ and ends at a third time $t_3$, e.g., ten seconds. Thus, the length of the third interval, in the exemplary embodiment shown, is six seconds. Moreover, the fourth interval commences at the third time $t_3$ and ends at a fourth time $t_4$.

It is the intent of the present invention to establish profiles of the four intervals which are within limits that may depend on the particular patient. Stated differently, it is the intent of the present invention to establish time rates of change for electrode 68 temperature at various intervals of electrocautery which may depend on patient characteristics.

In the exemplary embodiment shown, as more fully disclosed below the microprocessor 94 controls the energization of the source 38 of electricity to maintain the time rate of change of electrode temperature in the first interval to be equal to or greater than a first lower slope limit "B" and to be less than or equal to a first upper slope limit "A". In the exemplary embodiment shown, the first lower slope limit "B" is equal to about fifteen degrees Fahrenheit per second (15° F./sec) and the first upper slope limit "A" is equal to about twenty degrees Fahrenheit per second (20° F./sec).

Also, the microprocessor 94 controls the energization of the source 38 of electricity to maintain the time rate of change of electrode temperature in the second interval to be equal to or greater than a second lower slope limit "D" and to be less than or equal to a second upper slope limit "C". In the exemplary embodiment shown, the second lower slope limit "D" is equal to about ten degrees Fahrenheit per second (10° F./sec) and the second upper slope limit "C" is equal to about twenty degrees Fahrenheit per second (20° F./sec).

Importantly, the values of the second lower slope limit "D" and the second upper slope limit "C" can vary with the characteristics of the particular patient being treated. For example, in one preferred embodiment, the values of the second lower slope limit "D" and the second upper slope limit "C" can be multiplied by a factor which is linearly related to the actual time rate of change of temperature during the first interval. This factor can be, e.g., the ratio of the difference between the average of the upper and lower limits "A", "B" and the lower limit "B" and the difference between the actual time rate of change of temperature in the first interval ($dT_1/dt$) and the first lower slope limit "B". In mathematical terms, factor=$(0.5(A+B)-B)/(dT_1/dt-B)$. Alternatively, the values of the second lower slope limit "D" and the second upper slope limit "C" can be determined by entering a table with the actual time rate of change of temperature in the first interval ($dT_1/dt$) as the entering argument. Still further, for each electrode type and size, a corresponding look-up table (or factor "f") can be provided. And, corresponding look-up tables (or factors "f") can be established for side branch applications and varicose vein application.

FIG. 8 shows that the microprocessor 94 controls the energization of the source 38 of electricity to maintain the time rate of change of electrode temperature in the third interval to be about equal to a constant predetermined slope, e.g., three degrees Fahrenheit per second (3° F./sec). Like the slope in the second interval, the slope in the third interval can be modified, if desired; based upon the previous actual temperature profile. The fourth interval is defined by an endpoint at the fourth time $t_4$ which in turn is established as disclosed below.

Now referring to FIG. 9, the operation of the microprocessor 94 in establishing the desired temperature profile shown in FIG. 8 can be appreciated. Commencing at start state 150, the microprocessor 94 moves to decision block 152, wherein the microprocessor 94 determines whether the current interval is the first interval. If so, the microprocessor 94 moves to block 154 to adjust the power setting of the source 38 of electricity as appropriate to maintain the actual time rate of change of electrode temperature (dT/dt) between the first lower and upper slope limits "B" and "A".

From block 154, or from decision block 152 if the test there was negative, the microprocessor 94 moves to decision block 156, wherein the microprocessor 94 determines whether the current interval is the second interval. If so, the microprocessor 94 moves to block 158 to establish the second upper and lower slope limits "C", "D" as described based upon the actual time rate of change of electrode temperature (dT/dt) (and, hence, based upon the patient's characteristics) in the first interval. Next, the microprocessor 94 moves to block 160 to adjust the power setting of the source 38 of electricity as appropriate to maintain the actual time rate of change of electrode temperature (dT/dt) in the second interval between the second lower and upper slope limits "D" and "C".

From block 160, or from decision block 156 if the test there was negative, the microprocessor 94 moves to decision block 162, wherein the microprocessor 94 determines whether the current interval is the third interval. If so, the microprocessor 94 moves to block 164 to adjust the power setting of the source 38 of electricity as appropriate to maintain the actual time rate of change of electrode temperature (dT/dt) in the third interval at a constant predetermined slope. From block 164, or from decision block 162 if the test there was negative, the microprocessor 94 moves to block 166 to maintain the power setting of the source 38 of electricity at the setting that was established as of the third time $t_3$.

Moving to decision block 168 the microprocessor 94 determines the endpoint of the fourth interval. In other words, at decision block 168 the microprocessor 94 determines when the fourth time $t_4$ has been reached.

As indicated in FIG. 9, the microprocessor 94 determines that the endpoint of the fourth interval has been reached when any one of three conditions occurs. First, the microprocessor 94 determines that the endpoint of the fourth interval has been reached when electrode temperature equals or exceeds a predetermined end temperature $T_{end}$, e.g., 180° F. Also, the microprocessor 94 determines that the endpoint of the fourth interval has been reached when the change of temperature ΔT from the third time $t_3$ and the time of the current test equals or exceeds a predetermined end temperature delta $\Delta T_{end}$, e.g., 15° F.

Moreover, the microprocessor 94 determines that the endpoint of the fourth interval has been reached when the differential temperature DT equals or exceeds a predetermined differential temperature $dT_{end}$, e.g., 8° F. in the past second. It is to be appreciated in light of the above discussion that in determining the differential temperature DT, the microprocessor 94 considers the change in electrode temperature in the immediately preceding second of time. In the event that the microprocessor 94 determines, at decision block 168, that the endpoint of the fourth interval has been reached, the microprocessor 94 ends at end state 170. Otherwise, the microprocessor 94 loops back to block 166 each, e.g., fiftieth of a second.

Figure 10:
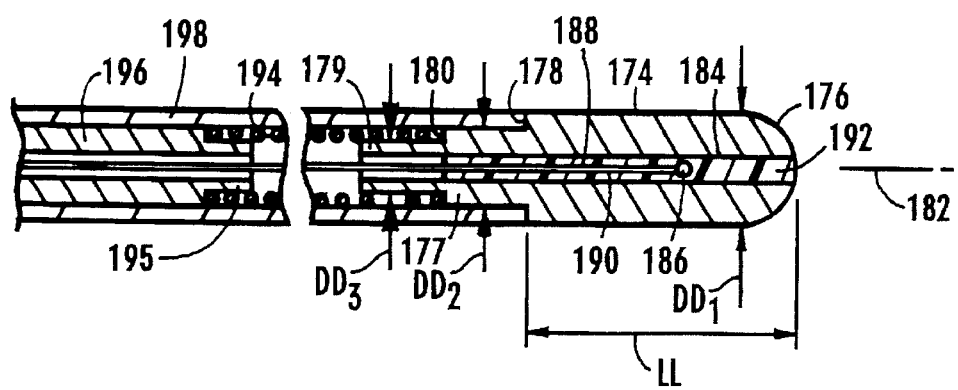
FIG. 10 is a cross-sectional view of an alternate embodiment of the electrode for in situ saphenous vein bypass applications, as would be seen along the line 5—5 in FIG. 1, with portions broken away for clarity.

Now referring to FIG. 10, an alternate embodiment of the electrode of the present invention for electro-ligation of saphenous vein side branches is shown, generally designated 172. As shown, the electrode 172 includes a hollow cylindrically-shaped electrode tip 174 which is made of type 304 stainless steel. FIG. 10 also shows that the tip 174 has an outside diameter $D_{D1}$ of about twenty eight thousandths of an inch (0.028").

The electrode tip 174 is formed with a rounded distal end 176. A medial cylindrical segment 177 having an outside diameter $D_{D2}$ that is slightly smaller than the outside diameter $D_{D1}$ of the tip 174 is formed integrally with the tip 174, and a ring-shaped abutment surface 178 is consequently established between the tip 174 and the medial segment 177. Likewise, a cylindrical proximal segment 179 having an outside diameter $D_{D3}$ that is slightly smaller than the outside diameter $D_{D2}$ of the medial segment 177 is formed integrally with the medial segment 177, and a proximal ring-shaped abutment surface 180 is consequently established between the medial segment 177 and the proximal segment 179. As shown, both abutment surfaces 178, 180 are orthogonal to the long axis 182 of the electrode 172. Furthermore, the length LL of the electrode tip 174 from the distal end 176 to the medial abutment surface 178 is about three hundred fifteen thousandths of an inch (0.315").

A cylindrical channel-like cavity 184 is established by the hollow tip 174, medial segment 177, and proximal segment 179. As shown, a temperature sensor, preferably a thermocouple 186, is disposed in the cavity 184. It can be appreciated in reference to FIG. 10 that the cavity 184 is enclosed by the wall of the tip 174, medial segment 177, and proximal segment 179.

As intended by the presently preferred embodiment, the thermocouple 186 is established by soldering together the distal ends of first and second electrically conductive wires 188, 190. FIG. 10 shows that the wires 188, 190 extend through the electrode 172. It is to be appreciated that an electrical signal is developed by the thermocouple 186 and transmitted through the wires 188, 190 to the electrical components disclosed above. This signal is representative of the temperature of the electrode 200. Consequently, the microprocessor 94 can receive a signal from the thermocouple 186 that is representative of the temperature of the electrode 172 and, hence, that is representative of the temperature of tissue in contact with the electrode 172. To hold and support the thermocouple 186, an epoxy material 192 fills the portion of the cavity 184 of the tip 174 that is not occupied by the thermocouple 186 and wires 188, 190.

Still referring to FIG. 10, a flexible spring 194, preferable made of stainless steel, is soldered to the proximal segment 179 and abuts the proximal abutment surface 180. The spring 194 is preferably closed-wound as shown, but it can be open wound. As intended by the present invention, the spring 194 establishes a flexible electrically conductive joining member which mechanically and electrically couples the electrode 172 with a distal projection 195 of a rigid stainless steel tube 196. Preferably, the spring 194 is soldered to the distal projection 195. In turn, the tube 196 with distal projection 195 is electrically connected to a source of electricity, such as the source 38 with feedback control device disclosed above, for energizing the electrode 172 through the tube 196 and spring 194.

As additionally shown in FIG. 10, an insulative sheath 198 surrounds the tube 196, spring 194, and medial segment 177, and the sheath 198 abuts the medial abutment surface 180. As can be seen in FIG. 10, the outer surface of the sheath 198 is flush with the outer surface of the electrode tip 174, and the sheath 198 is bonded to the medial segment 177 with a high-temperature epoxy. Like the sheath 82 shown in FIG. 5, the sheath 198 shown in FIG. 10 is made of an electrically resistive, smooth, biocompatible material, such as PEBAX®.

Figure 11:
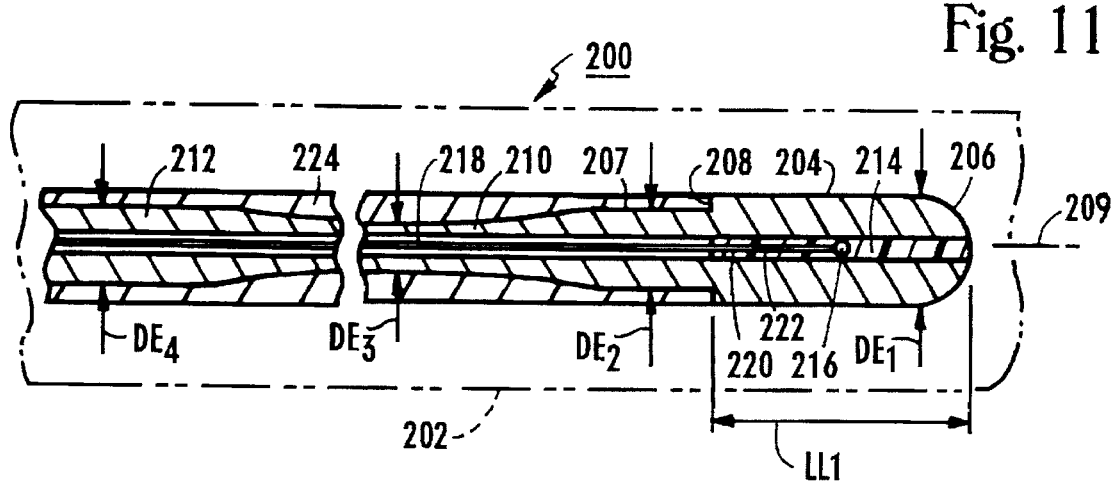
FIG. 11 a cross-sectional view of yet another alternate embodiment of the electrode for varicose vein treatment applications, as would be seen along the line 5—5 in FIG. 1, with portions broken away for clarity and with a delivery catheter shown in phantom.

In addition to the saphenous vein bypass application of the present invention, it is to be understood that the present invention can be used to less-invasively treat varicose veins by electro-ligation. FIG. 11 shows an electrode, generally designated 200, that can be used for such an application by advancing a delivery catheter 202 in which the electrode 200 is disposed into a varicose vein of a patient's leg through a small percutaneous incision, and then activating the electrode 200 to electrically ligate the vein. In one presently preferred embodiment, the delivery catheter 202 is the endoscope disclosed in U.S. Pat. No. 5,318,526 for an invention entitled "Flexible Endoscope with Hypotube Activating Wire", owned by the assignee of the present invention and incorporated herein by reference.

As shown in FIG. 11, the electrode 200 includes a hollow cylindrically-shaped electrode tip 204 which is made of type 304 stainless steel. FIG. 11 also shows that the tip 204 has an outside diameter $D_{E1}$ of about twenty eight thousandths of an inch (0.028").

The electrode tip 204 is formed with a rounded distal end 206. A medial cylindrical segment 207 having an outside diameter $D_{E2}$ of about eighteen thousandths of an inch (0.018") is formed integrally with the tip 204, and a ring-shaped abutment surface 208 is consequently established between the tip 204 and the medial segment 207. As shown, the abutment surface 208 is orthogonal to the long axis 209 of the electrode 200. The length $LL_1$ of the electrode tip 204 from the distal end 206 to the abutment surface 208 is about three hundred fifteen thousandths of an inch (0.315").

FIG. 11 shows that the medial segment 207 tapers proximally radially inwardly to a hollow tubular joining member 210 having an outside diameter $D_{E3}$ of about fourteen thousandths of an inch (0.014"). In turn, the joining member 210 tapers proximally radially outwardly to a hollow electrode tube 212 having an outside diameter $D_{E4}$ of about sixteen thousandths of an inch (0.016"). Preferably, the joining member 210, tube 212, and medial segment 207 are formed integrally together and are made of stainless steel. The tube 212 is electrically connected to a source of electricity, such as the source 38 with feedback control device disclosed above, for energizing the electrode 200.

A cylindrical channel-like cavity 214 is established by the hollow tip 204, medial segment 207, joining member 210, and tube 212. As shown, a temperature sensor, preferably a thermocouple 216, is disposed in the cavity 214. It can be appreciated in reference to FIG. 11 that the cavity 214 is enclosed by the wall of the tip 204, medial segment 207, joining member 210, and tube 212.

As intended by the presently preferred embodiment, the thermocouple 216 is established by soldering together the distal ends of first and second electrically conductive wires 218, 220. FIG. 11 shows that the wires 218, 220 extend through the electrode 200. It is to be appreciated that an electrical signal is developed by the thermocouple 216 and transmitted through the wires 218, 220 to the electrical components disclosed above. This signal is representative of the temperature of the electrode 200. Consequently, the microprocessor 94 can receive a signal from the thermocouple 216 that is representative of the temperature of the electrode 200 and, hence, that is representative of the temperature of tissue in contact with the electrode 200. To hold and support the thermocouple 216, an epoxy material 222 fills the portion of the cavity 214 of the tip 204 that is not occupied by the thermocouple 216 and wires 218, 220.

As additionally shown in FIG. 11, an insulative sheath 224 surrounds the structure discussed above, and the sheath 224 abuts the abutment surface 208. As can be seen in FIG. 11, the outer surface of the sheath 224 is flush with the outer surface of the electrode tip 204, and the sheath 224 is bonded to the medial segment 207 with a high-temperature epoxy. Like the sheath 82 shown in FIG. 5, the sheath 224 shown in FIG. 11 is made of an electrically resistive, smooth, biocompatible material, such as PEBAX®.

Figure 12:
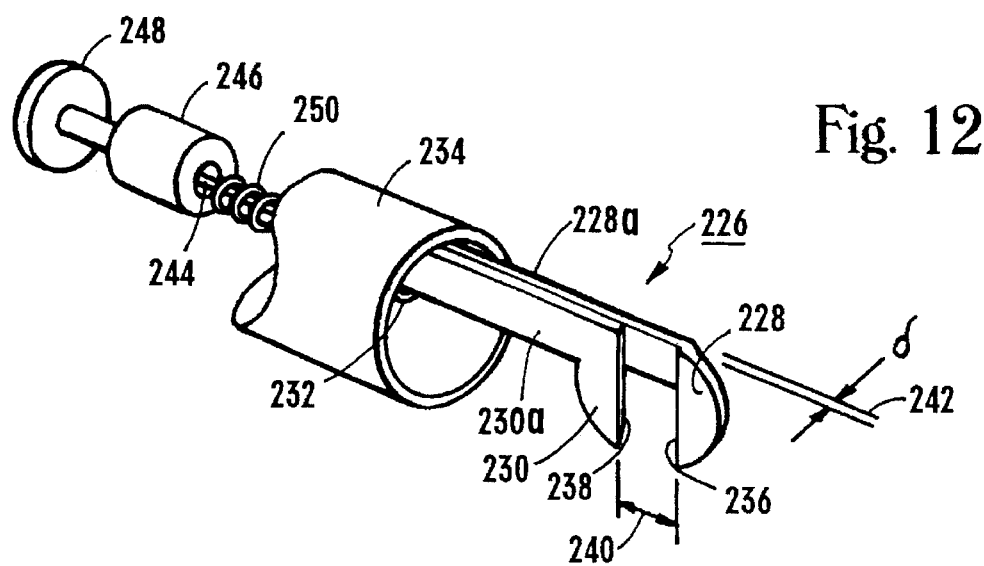
FIG. 12 is a perspective view of an alternate embodiment of the valvulotome of the present invention, with the blades in the open position.

Referring now to FIG. 12, an alternate embodiment of the valvulotome of the present invention is shown, generally designated 226. As shown, the valvulotome 226 includes a fixed blade 228 and a movable blade 230. More particularly, the valvulotome 226 can be disposed in a lumen 232 of a catheter 234 that can inserted into an endoscope or other catheter, e.g., the operating catheter 20 or control catheter 22 shown in FIG. 3. A shaft 228A of the fixed blade 228 is bonded or otherwise fixedly attached to the catheter 234, and a shaft 230A of the movable blade 230 is reciprocally disposed in the lumen 232 and is closely supported thereby.

FIG. 12 shows that the fixed blade 228 defines a fixed sharpened cutting edge 236, while the movable blade 230 defines a sharpened movable cutting edge 238 facing the fixed blade 228. It can readily be appreciated in reference to FIG. 12 that the movable cutting edge 238 is reciprocally movable in the directions indicated by the indicator 240 between a closed position, wherein the blades 228, 230 are closely juxtaposed, and the open position shown in FIG. 12, wherein the blades 228, 230 are spaced apart for receiving tissue therebetween. As shown in FIG. 12, to permit the cutting edges 236, 238 to contact each other when the blades 228, 230 are in the closed position and thereby cut tissue that is between the blades 228, 230, the fixed cutting edge 236 is slightly offset, by a distance δ, from the centerline 242 of the shaft 228A of the fixed blade 228. Both cutting edges 236, 238 can be sharpened by, e.g., grinding techniques known in the art.

FIG. 12 moreover shows that an activating wire 244 is reciprocally disposed in the catheter 234. It is to be understood that the activating wire 244 is fixedly attached by means well-known in the art to the shaft 230A of the movable blade 230. The wire 244 extends through an operating handle 246 and is attached to a manipulable handle 248. Consequently, the wire 244 and, hence, movable cutting blade 230 can be moved relative to the fixed blade 228 by appropriately manipulating the manipulable handle 248. If desired, a biasing spring 250 can be engaged in accordance with principles well-known in the art to the wire 244 and operating handle 246 to urge the wire 244 proximally or distally, as appropriate, and thereby bias the movable blade 230 to the closed or open position, as desired.

While the particular apparatus for in situ saphenous vein bypass and less-invasive varicose vein treatment as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

TABLE 1

| Z3(Ohms) | Z2(Ohms) |
| --- | --- |
| 0–49 | 0 |
| 50–74 | 200 |
| 75–99 | 225 |
| 100–124 | 300 |
| 125–149 | 350 |
| 150–174 | 400 |
| 175–199 | 425 |
| 200–224 | 500 |
| 225–249 | 550 |
| 250–274 | 575 |
| 275–299 | 600 |
| 300–324 | 625 |
| 325–349 | 650 |
| 350–374 | 675 |
| 375–449 | 700 |
| 450–474 | 725 |
| 475–499 | 750 |
| 500–524 | 775 |
| 525–549 | 800 |
| 550–574 | 825 |
| 575–599 | 850 |
| 600–799 | 900 |
| 800–999 | 999 |

What is claimed is:

1. A device for electro-ligation of a blood vessel, comprising:

a delivery catheter having a distal end;

an optical image fiber positioned in the delivery catheter for generating an image of structure beyond the distal end of the delivery catheter;

a hollow electrode defining a cavity and disposed in the delivery catheter, the electrode being selectively advanceable beyond the distal end for cauterizing tissue;

a valvulotome juxtaposed with the distal end of the delivery catheter to cut valves within the saphenous vein; and a temperature sensor disposed in the cavity of the electrode for sensing the temperature thereof.

2. The device of claim 1, wherein the temperature sensor includes a thermocouple and two electrical wires attached to the thermocouple.

3. The device of claim 2, further comprising an epoxy material disposed in the cavity.

4. The device of claim 3, wherein the delivery catheter is an endoscope, and the endoscope is advanceable into a varicose vein for cauterizing the varicose vein in situ.

5. The device of claim 3, wherein the delivery catheter is an operating catheter advanceable into a patient for cauterizing a side branch of a saphenous vein in situ, and the device further comprises a flexible electrically conductive joining member connected to the electrode for transmitting electricity thereto.

6. The device of claim 4, wherein the flexible joining member is a closed wound spring.

7. The device of claim 1, wherein the valvulotome includes a fixed blade defining a fixed cutting edge and a movable blade defining a movable cutting edge facing the fixed blade, the movable cutting edge having a closed position, wherein the blades are closely juxtaposed, and an open position, wherein the blades are spaced apart for receiving tissue therebetween.

8. The device of claim 1, further comprising:

a source of electricity electrically connected to the electrode, the source of electricity having a variable power output such that the source of electricity can be energized to energize the electrode to thereby cause the lumen of the blood vessel to collapse when the electrode is positioned in the vessel; and a feedback device electrically connected to the source of electricity, the feedback device including a microprocessor and a sensor for sensing at least one parameter and generating a respective parameter signal in response thereto, the microprocessor including:

a comparator for receiving the parameter signal and comparing the parameter signal to a setpoint having a value dependent upon at least one of: electrical output parameters of the source of electricity, time rate of change of electrode temperature, and power output of the source of electricity, wherein the comparator generates a control signal in response to cause the microprocessor to control the power output of the source of electricity.

9. An apparatus for stopping blood flow through a blood vessel, comprising:

a delivery catheter having a distal end percutaneously positionable in the vessel;

an electrode disposed in the delivery catheter and selectively advanceable beyond the distal end of the delivery catheter for facilitating electrocautery of tissue to thereby stop blood flow from the tissue;

a valvulotome juxtaposed with the electrode to cut valves in the blood vessel;

a temperature sensor disposed in the electrode for generating a temperature signal representative of the temperature thereof; and a light transmitting member disposed in the delivery catheter for generating an image of an object located beyond the distal end of the catheter for facilitating electrocautery.

10. The apparatus of claim 9, wherein the light transmitting member is an optical fiber, and the optical fiber is removably disposed in the delivery catheter for replacement of the optical fiber in another like catheter.

11. The apparatus of claim 10, further comprising:

a source of electricity connected to the electrode; and a feedback device electrically connected to the source of electricity, the feedback device for sensing at least one preselected parameter selected or derived from the group of parameters consisting of: electrode temperature, source of electricity output voltage, time rate of change of source of electricity output voltage, source of electricity output current, time rate of change of source of electricity output current, source of electricity output power, time rate of change of source of electricity output power, vessel electrical impedance, time rate of change of vessel electrical impedance, capacitive current, the feedback device generating a parameter signal in response thereto.

12. The apparatus of claim 11, wherein the feedback device includes:

a comparator for receiving the parameter signal and comparing the parameter signal to a setpoint having a value dependent upon at least one of: electrical output parameters of the source of electricity, time rate of change of electrode temperature, and power output of the source of electricity, wherein the comparator generates a control signal in response for controlling the power output of the source of electricity.

13. The apparatus of claim 12, wherein the valvulotome includes a fixed blade defining a fixed cutting edge and a movable blade defining a movable cutting edge facing the fixed blade, the movable cutting edge having a closed position, wherein the blades are closely juxtaposed, and an open position, wherein the blades are spaced apart for receiving tissue therebetween.

14. The apparatus of claim 12, wherein the temperature sensor includes a thermocouple and two electrical wires attached to the thermocouple.

15. The apparatus of claim 14, wherein the electrode is formed with a cavity for holding the temperature sensor, and the apparatus further comprises an epoxy material disposed in the cavity.

16. The apparatus of claim 15, wherein the delivery catheter is an operating catheter advanceable into a patient for cauterizing a side branch of a saphenous vein in situ, and the apparatus further comprises a closed wound spring connected to the electrode for transmitting electricity thereto.

17. The apparatus of claim 15, wherein the delivery catheter is an endoscope, and the endoscope is advanceable into a varicose vein for cauterizing the varicose vein in situ.

* * * * *